(12) United States Patent
Callaghan et al.

(10) Patent No.: US 11,446,463 B2
(45) Date of Patent: Sep. 20, 2022

(54) DEVICES, SYSTEMS, AND METHODS FOR APPLYING POSITIVE END EXPIRATORY PRESSURE

(71) Applicant: ONEBREATH, INC., Palo Alto, CA (US)

(72) Inventors: Matthew John Callaghan, Palo Alto, CA (US); Lawrence Edward Miller, Palo Alto, CA (US); Edward Ayrapetian, Palo Alto, CA (US)

(73) Assignee: ONEBREATH, INC., Palo Alto, CA (US)

( * ) Notice: Subject to any disclaimer, the term of this patent is extended or adjusted under 35 U.S.C. 154(b) by 568 days.

(21) Appl. No.: 15/516,611

(22) PCT Filed: Oct. 7, 2015

(86) PCT No.: PCT/US2015/054527
§ 371 (c)(1),
(2) Date: Apr. 3, 2017

(87) PCT Pub. No.: WO2016/057694
PCT Pub. Date: Apr. 14, 2016

(65) Prior Publication Data
US 2017/0246420 A1 Aug. 31, 2017

Related U.S. Application Data

(60) Provisional application No. 62/060,945, filed on Oct. 7, 2014.

(51) Int. Cl.
*A61M 16/20* (2006.01)
*A61M 16/08* (2006.01)
(Continued)

(52) U.S. Cl.
CPC ...... *A61M 16/203* (2014.02); *A61M 16/0063* (2014.02); *A61M 16/024* (2017.08);
(Continued)

(58) Field of Classification Search
CPC ........ A61M 16/0063; A61M 2205/502; A61M 2205/3375; A61M 2205/3368;
(Continued)

(56) References Cited

U.S. PATENT DOCUMENTS 4,905,685 A  3/1990 Olsson et al.
5,002,050 A  3/1991 McGinnis et al.
(Continued)

OTHER PUBLICATIONS

International Search Report and Written Opinion from International Application No. PCT/US2015/054518 dated Jan. 11, 2016.
(Continued)

*Primary Examiner* — LaToya M Louis
(74) *Attorney, Agent, or Firm* — Dorsey & Whitney LLP

(57) ABSTRACT

Embodiments disclosed herein are directed to ventilation devices, systems, and methods for applying positive end expiratory pressure (PEEP) to the lungs of a patient. For example, applying above atmospheric pressure to the lungs of the patient may mitigate alveolar collapse in the lungs and/or may have other health benefits for the patient.

23 Claims, 4 Drawing Sheets

(51) Int. Cl.
*A61M 16/00* (2006.01)
*A61M 16/12* (2006.01)
*A61M 16/10* (2006.01)

(52) U.S. Cl.
CPC .... *A61M 16/0866* (2014.02); *A61M 16/0883* (2014.02); *A61M 16/1005* (2014.02); *A61M 16/12* (2013.01); *A61M 16/208* (2013.01); *A61M 16/204* (2014.02); *A61M 2016/0027* (2013.01); *A61M 2016/0039* (2013.01); *A61M 2016/102* (2013.01); *A61M 2202/0208* (2013.01); *A61M 2205/3331* (2013.01); *A61M 2205/3368* (2013.01); *A61M 2205/3375* (2013.01); *A61M 2205/502* (2013.01)

(58) Field of Classification Search
CPC .. A61M 2205/3331; A61M 2202/0208; A61M 2016/102; A61M 2016/0039; A61M 2016/0027; A61M 16/208; A61M 16/204; A61M 16/203; A61M 16/12; A61M 16/1005; A61M 16/0883; A61M 16/0866; A61M 16/024
See application file for complete search history.

(56) References Cited

U.S. PATENT DOCUMENTS

| | | |
|---|---|---|
| 5,383,449 A | 1/1995 | Forare et al. |
| 5,558,083 A | 9/1996 | Bathe et al. |
| 5,918,597 A | 7/1999 | Jones et al. |
| 2008/0053438 A1 | 3/2008 | Devries et al. |
| 2009/0183737 A1 | 7/2009 | Oberle et al. |
| 2010/0252046 A1 | 10/2010 | Dahlström et al. |
| 2011/0088697 A1 | 4/2011 | DeVries et al. |
| 2011/0132366 A1 | 6/2011 | Ogilvie et al. |
| 2011/0209702 A1 | 9/2011 | Vuong et al. |
| 2011/0247411 A1 | 10/2011 | Speldrich et al. |
| 2014/0261426 A1 | 9/2014 | Ahmad et al. |
| 2014/0283828 A1 | 9/2014 | Acker et al. |
| 2015/0107585 A1 | 4/2015 | Allum |
| 2016/0051780 A1* | 2/2016 | Sherman ............ A61M 16/024 128/204.21 |

OTHER PUBLICATIONS

International Search Report and Written Opinion from International Application No. PCT/US2015/054527 dated Dec. 31, 2015.
Non-Final Office Action for U.S. Appl. No. 15/516,502 dated May 16, 2019.

* cited by examiner

DEVICES, SYSTEMS, AND METHODS FOR APPLYING POSITIVE END EXPIRATORY PRESSURE

CROSS-REFERENCE TO RELATED APPLICATIONS

This application claims priority to U.S. Provisional Application No. 62/060,945 filed on 7 Oct. 2014, the disclosure of which is incorporated herein, in its entirety, by this reference.

BACKGROUND

Generally, a medical ventilator may be used to supply or force breathable gas (e.g., an air-oxygen mixture) into the lungs of a patient. In some instances, positive end expiratory pressure (PEEP) may be used in ventilation. PEEP is used to prevent complete alveolar collapse during exhalation, which can improve hypoxemia and limit lung damage in patients with acute respiratory distress.

PEEP is typically applied to the airway by use of a mechanical valve, an electronically-controlled threshold valve, or positive airflow into the ventilator breathing circuit. Since PEEP is applied to the exhale phase of ventilation, the mechanism used to create PEEP is often in communication with the exhaled air path. Commonly, materials and components in communication with exhaled patient air are required to be cleaned or sterilized and replaced often. Using relatively expensive and accurate proportional valve may be cost prohibitive in some circumstances.

Accordingly, users and manufacturers of ventilation devices and systems continue to seek improvements to accuracy and cost of such ventilation devices.

SUMMARY

Embodiments disclosed herein are directed to ventilation devices, systems, and methods for applying positive end expiratory pressure (PEEP) to lungs of a patient. For example, as the patient exhales, the ventilation system may apply pressure to the lungs, which may be above the atmospheric pressure (e.g., 4-5 $cmH_2O$ or >5 $cmH_2O$). Applying above atmospheric pressure to the lungs of the patient may mitigate alveolar collapse in the lungs and/or may have other health benefits for the patient.

An embodiment includes a system for applying PEEP in ventilation of lungs of a patient. The system includes an exhalation line configured to be in fluid communication with the lungs of the patient and to receive exhaled gas from the lungs of the patient. The system also includes a diaphragm valve coupled to the exhalation line and configured restrict fluid flow therefrom, thereby applying positive end expiratory pressure during exhalation of air from the lungs of the patient, in response to a control pressure applied at an actuator of the diaphragm valve. Moreover, the system includes an actuator line coupling the diaphragm valve to a source of pressurize fluid, and an electrically-controllable valve coupled to the actuator line and controlling the pressure applied by fluid from the source of pressurized fluid to the actuator of the diaphragm valve. The system further includes a controller operably coupled to the electrically-controllable valve and configured to change the positive end expiratory pressure by directing operation of the electrically-controllable valve.

Embodiments also include an additional or alternative system for applying PEEP in ventilation of lungs of a patient. The system includes an exhalation line configured to be in fluid communication with the lungs of the patient and to receive exhaled gas from the lungs of the patient, and a pressure-operated valve coupled to the exhalation line and configured restrict fluid flow therefrom, thereby applying positive end expiratory pressure during exhalation of air from the lungs of the patient, in response to a control pressure applied on an actuator of the pressure-operated valve. In addition, the system includes an actuator line coupling the pressure-operated valve control to a source of pressurized breathable gas and configured to supply the pressurized breathable gas to apply the control pressure on the actuator of the pressure-operated valve. The system also includes an inhalation line coupleable to the source of pressurized breathable gas to supply the breathable gas into the lungs of the patient, and a supply valve coupleable to the source of pressurized breathable gas and coupled to the actuator line and to the inhalation line and configured to control supply of the pressurized breathable gas thereto.

At least one embodiment includes a method for controlling application of PEEP in ventilation of lungs of a patient. The method includes placing a pressurizable channel in fluid communication with the lungs of the patient for accepting exhaled gas therefrom, and operating a pressure-controllable valve to control flow of the exhaled gas in the pressurizable channel by applying pressure at an actuator of the pressure-controlled valve. The method also includes controlling a solenoid valve to apply the pressure at the actuator of the pressure-controlled valve.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments, wherein identical reference numerals refer to identical or similar elements or features in different views or embodiments shown in the drawings.

DETAILED DESCRIPTION

Figure 1:
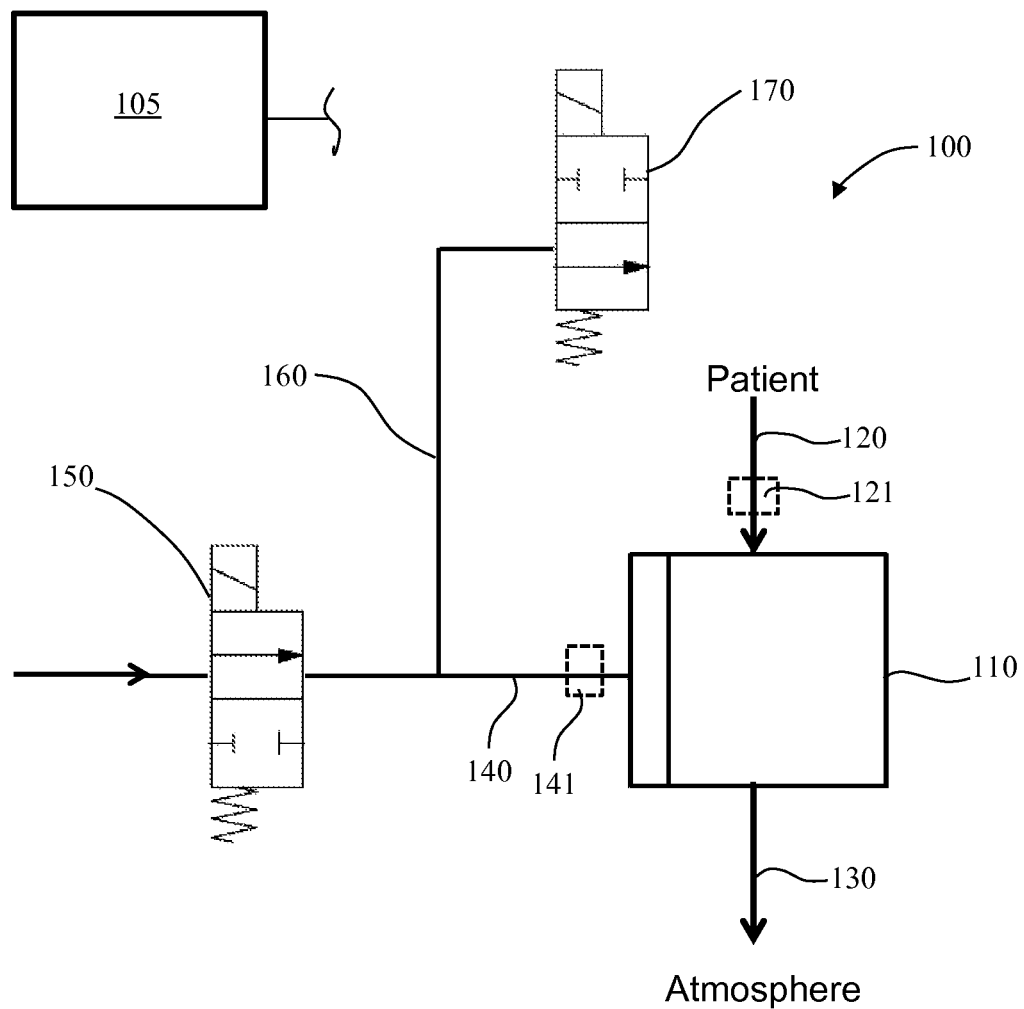
FIG. 1 is a schematic diagram of a system for applying positive end exhalation pressure to lungs of a patient, according to an embodiment.

Embodiments disclosed herein are directed to ventilation devices, systems, and methods for applying positive end expiratory pressure (PEEP) to lungs of a patient.

For example, as the patient exhales, the ventilation system may apply pressure to the lungs, which may be above the atmospheric pressure (e.g., 4-5 $cmH_2O$ or >5 $cmH_2O$). Applying above atmospheric pressure to the lungs of the patient may mitigate alveolar collapse in the lungs and/or may have other health benefits for the patient.

In some embodiments, the ventilation system may include a pressure-operated or pressure-controlled valve that may control the end expiratory pressure applied to the lungs of the patient (e.g., at the time when the patient exhales). For example, a diaphragm valve or a pilot-operated diaphragm valve may restrict exhalation by the patient, thereby producing positive (e.g., above atmospheric) pressure in the lungs as the patient exhales. Moreover, the system may control one or more of initiation and termination of the positive pressure, duration of the positive pressure, or the amount or magnitude of positive pressure applied to the lungs of the patient.

In an embodiment, the pressure-operated valves may be relatively inexpensive and/or disposable. For example, during operation, the valve may be contaminated with bodily fluids of the patient and may not be suitable for use with another patient (e.g., without sterilization). The pressure-operated valve may be removed and/or discarded before the system is used with another patient, and a replacement (e.g., new and/or sterilized) pressure-operated valve may be connected in the system.

Generally, the diaphragm valve may be controlled by an actuator that may be operated by any number of suitable mechanisms (e.g., manually, pneumatically, hydraulically, electrically, etc.). In particular, the actuator may multiple ports in fluid communication with one another (e.g., two ports) and a membrane that may be moved and/or flexed by the actuator to restrict flow between two or more of the ports. For example, the actuator may move the membrane from a first position (e.g., where the diaphragm valve is open and the flow between two ports thereof is generally unrestricted) to a second position (e.g., where the diaphragm valve is at least partially closed and the flow between the two ports is at least partially restricted). As described below in more detail, pressure (e.g., above atmospheric pressure) may be applied to the actuator that, in response to the applied pressure, may move the diaphragm of the valve to a suitable and/or selected location, thereby defining a selected or suitable opening through the valve. In some embodiments, the diaphragm may be generally biased, such that when the actuator experience atmospheric pressure and/or below atmospheric pressure, the diaphragm defines a maximum opening through the valve.

In an embodiment, the patient may exhale into an exhalation port that may be coupled to a pressurizable channel (e.g., a lumen of a tube) through which the exhaled gas may flow toward the atmosphere. The pressure-operated valve (e.g., diaphragm valve) may be coupled to the pressurizable channel and may restrict flow therethrough, thereby increasing pressure in the pressurizable channel and in the lungs of the patient (which are in fluid communication with the pressurizable channel via the exhalation port) as the patient exhales. Specifically, for example, the pressure-operated valve may be operated by applying pressure to the actuator to constrict the flow between the inlet and outlet ports of the diaphragm valve (thereby increasing exhalation pressure) and may be further operated to reduce and/or remove constriction between the inlet and outlet ports by reducing or removing the pressure applied to the actuator (thereby decreasing the exhalation pressure, such that the pressure applied to the lungs of the patient is generally the atmospheric pressure).

FIG. 1 is a schematic illustration of a PEEP system 100 for applying positive end expiratory pressure during ventilation of the lungs of a patient, according to an embodiment. The PEEP system 100 may include a pressure-operated valve, such as a diaphragm valve 110, which may control exhalation (e.g., exhalation pressure) and corresponding pressure in the lungs of the patient. For example, an exhalation line 120 may be in fluid communication with the lungs of the patient (e.g., via a ventilator mask or other device) and may be coupled to the diaphragm valve 110, such that as the patient exhales, the exhaled gas may enter the exhalation line 120 and flow therein toward the diaphragm valve 110. In addition to the exhalation line 120, the diaphragm valve 110 may be coupled to and/or may include an outlet port or outlet line 130 that may be open to and/or may be in fluid communication with the atmosphere. Specifically, the exhaled gas may flow from the exhalation line 120, through the diaphragm valve 110 and out of the outlet line 130 to the atmosphere.

Generally, the exhalation line 120 may have any suitable shape and/or size (e.g., cross-sectional size or area of the cross-section). In an embodiment, the cross-sectional size of the exhalation line 120 may be such that during the exhalation, the lungs of the patient experience no significant positive pressure. Alternatively, the exhalation line 120 may have any suitable cross-sectional size, such as to produce or apply a suitable and/or selected positive pressure on the lungs of the patient.

Moreover, in some embodiments, the cross-sectional size (e.g., area) of the outlet line 130 may be equal to or greater than the cross-sectional size of the exhalation line 120. Also, the cross-sectional area of the passageway in the diaphragm valve 110 may be equal to or greater than the cross-sectional area of the exhalation line 120 and/or the cross-sectional area of the outlet line 130. Hence, for example, when the diaphragm valve 110 is fully open, the diaphragm valve 110 may have substantially no effect on the pressure applied to the lungs of the patient during exhalation (e.g., as the patient exhales, the pressure in the lungs of the patient may rapidly approach atmospheric pressure). For example, the pressure applied on the lungs of the patient during the exhalation may be atmospheric pressure (e.g., when the exhalation line 120 does not restrict exhalation in a manner that would apply pressure on the lungs of the patient). Alternatively or additionally, when the diaphragm valve 110 is fully open, the pressure applied to the lungs of the patient may be a predetermined pressure, which may be produced or applied by a suitably sized exhalation line 120.

In an embodiment, to change or increase the pressure applied onto the lungs of the patient by the PEEP system 100, the diaphragm valve 110 may be at least partially closed. For example, partially closing a diaphragm of the diaphragm valve 110 may restrict flow from the exhalation line 120 to the outlet line 130, thereby increasing pressure applied to the lungs when the patient exhales. In some embodiments, the diaphragm valve 110 may be operated to close the diaphragm in a manner that produces a selected amount of positive pressure on the lungs of the patient during exhalation.

In an embodiment, the diaphragm of the diaphragm valve 110 may be controlled by applying hydraulic or pneumatic pressure (e.g., control pressure) to an actuator of the diaphragm in the diaphragm valve 110. It should be appreciated that the pressure applied to the actuator may be produced by a compressible or an incompressible fluid (e.g., by a gas, such as a breathable gas, and/or by a liquid). For example, in response to the applied pressure, the actuator may move the diaphragm of the diaphragm valve 110 to restrict the flow through the diaphragm valve 110. An actuator line 140 may be in fluid communication with the actuator of the diaphragm valve 110, such that changing the pressure in the actuator line 140 may produce a change in the pressure applied to the actuator and a corresponding change in the opening of the diaphragm valve 110. As described above, changing the opening in the diaphragm valve 110 may produce a corresponding change in the pressure applied to the lungs of the patient during exhalation.

The actuator line 140 may receive a pressurized fluid (e.g., a pressurized gas) from a source of pressurized fluid, such as a tank or container, an accumulator, a compressor, etc. In some embodiments, the PEEP system 100 may include a supply valve 150 that may control fluid flow from the source of pressurized fluid into the actuator line 140. Specifically, for example, the supply valve 150 may control the pressure of the fluid in the actuator line 140 and the pressure applied to the actuator of the diaphragm of the diaphragm valve 110, thereby controlling the position of the actuator and the diaphragm in the diaphragm valve 110.

For example, the supply valve 150 may be closed and the pressure in the actuator line 140 may be such that the diaphragm valve remains unmoved and the diaphragm valve 110 is in fully open configuration. In some embodiments, when the pressure in the actuator line 140 is at approximately atmospheric pressure the diaphragm valve 110 may be fully open. For example, the pressure applied onto the diaphragm valve from the outlet line 130 (e.g., atmospheric pressure) and/or the pressure in the exhalation line 120 (e.g., the pressure applied by the exhaled gas from the lungs of the patient) may position the diaphragm valve 110 at a location that defines a maximum opening of the diaphragm valve 110 (e.g., such that the diaphragm valve is in the fully open configuration). Additionally or alternatively, the diaphragm of the diaphragm valve 110 may be biased, such that when the pressure in the actuator line 140 is below a threshold pressure (e.g., the threshold pressure may be pressure suitable or required to overcome the biasing of the diaphragm valve), the diaphragm may remain in and/or return to a location of the open configuration of the diaphragm valve 110. In any event, when the fluid in the actuator line 140 is at a first pressure, which may be any suitable pressure, the diaphragm valve 110 may be in a first position, such that the diaphragm valve 110 is fully open.

In an embodiment, increasing the pressure in the actuator line 140 from the first pressure to a second pressure may advance or move the diaphragm valve in the diaphragm valve 110, thereby at least partially closing the diaphragm valve 110 and restricting flow from the exhalation line 120 through the diaphragm valve 110. As described above, restricting flow through the diaphragm valve 110 may apply a positive pressure to the lungs of the patient during exhalation. Hence, the pressure in the actuator line 140 may be increased to any suitable pressure to produce a corresponding closing of the diaphragm valve 110 and increase in exhalation pressure in the lungs of the patient.

In some embodiments, the positive pressure applied to the lungs of the patient may be decreased by increasing the opening in the diaphragm valve 110, thereby allowing the exhaled gases to pass through the diaphragm valve 110 more freely. For example, the PEEP system 100 may include a vent that may selectively release at least some of the fluid in the actuator line 140, thereby reducing the pressure therein and reducing the pressure experienced by the actuator of the diaphragm valve 110. As mentioned above, reducing the pressure applied to the diaphragm of the diaphragm valve 110 may allow the diaphragm of the diaphragm valve 110 to move or reposition to a location that defines a larger opening through the diaphragm valve 110 (e.g., as compared before reducing the pressure). In an embodiment, venting line 160 may be fluid communication with the actuator line 140 at a location along the actuator line 140 between the supply valve 150 and the actuator of the diaphragm valve 110 and/or near the actuator of the diaphragm valve 110. Moreover, the venting line 160 may terminate at a venting valve 170, which may be operated to permit or restrict flow of fluid out of the venting line 160.

When the venting valve 170 is closed, opening the supply valve 150 may pressurize the actuator line 140 and apply pressure to the diaphragm of the diaphragm valve 110. By contrast, for example, at least partially opening the venting valve 170 may allow at least some of the fluid in the actuator line 140 to flow through the venting line 160 and out of the venting valve 170 (e.g., into the atmosphere), thereby reducing the pressure applied to the actuator of the diaphragm valve 110 (e.g., to a selected pressure, to atmospheric pressure). Hence, permitting fluid to flow out of the actuator line 140 and, for example, out into the atmosphere, may reduce the pressure in the actuator line 140, thereby moving or allowing the diaphragm of the diaphragm valve 110 to move to location that defines a greater opening through the diaphragm valve 110 (e.g., as compared to the location before pressure reduction). As described above, increasing the opening through the diaphragm valve 110 may reduce the positive pressure applied to the lungs of the patient. In an embodiment, the supply valve 150 may be at least partially closed and/or the opening through the supply valve 150 may be reduced before opening the venting valve 170 to allow the fluid in the actuator line 140 to exit therefrom, which may reduce the pressure applied to the lungs of the patient to the atmospheric pressure.

In some embodiments, the supply valve 150 and/or the venting valve 170 may be electronically controlled. For example, the supply valve 150 and/or the venting valve 170 may be solenoid valves, such as standard solenoid valves (e.g., valves that may have only two positions—open and closed) or proportional solenoid valves, which may progressively close or open in a proportion to a signal applied thereto (e.g., proportional to a voltage, amperage, etc., applied to the valve). Accordingly, for example, a controller 105 may operate the supply valve 150 and/or the venting valve 170 to regulate the positive end expiratory pressure applied to lungs of the patient.

Generally, the controller 105 may include a processor, and I/O interface, and a memory coupled to the processor and including instructions to perform acts or steps for operating component(s) of the PEEP system 100 according to one or more of the embodiments described herein. Additionally or alternatively, the controller 105 may include field programmable gate arrays (FPGAs) that may be configured or programmed to perform one or more acts or steps for operating component(s) of the PEEP system 100 according to one or more embodiments described herein. For example, one or more of the sensors described herein may be operably coupled to the controller 105 at the I/O interface thereof, such that the controller 105 may receive signal from the sensor(s). The controller 105 may process the received signals according to one or more embodiments (e.g., the controller 105 may include A/D converter and may convert analog signals to one or more digital signals, such that the processor may perform one or more acts or steps according to one or more embodiments described herein).

In some embodiments, the controller 105 may include an interface that may accept an input from a user, which may be related to a desired a suitable positive end expiratory pressure to be applied to the lungs of the patient. The user may input the positive and expiratory pressure into the controller 105, and the controller 105 may direct operation of and/or operate the supply valve 150 and/or venting valve 170 to regulate the positive and expiratory pressure applied to the lungs of the patient, which may be based at least partially on the input received by the controller 105. For example, the user may input the positive and expiratory pressure into the user interface of the controller 105, such as via a touch screen, keypad, or other suitable user interface. For example, the controller 105 may be calibrated based on a particular elements and components of the PEEP system 100 (e.g., the diaphragm valve 110, the cross-sectional sizes of the exhalation line 120 and/or outlet line 130, the pressure at the source of pressurized fluid, etc.) to produce the positive end expiratory pressure input by a user into the controller 105.

In an embodiment, the PEEP system 100 may include a pressure sensor 121 that may be located in the exhalation line 120 and/or may be in fluid communication with the exhalation line 120 (e.g., the pressure sensor 121 may be positioned near an opening in the diaphragm valve 110). Generally, the pressure sensor 121 may be any suitable pressure sensor, such as a piezoelectric pressure sensor, pressure transducer, piezoresistive pressure sensor, capacitive pressure sensor, MEMS pressure sensor, LVDT pressure sensor, or combinations thereof. Moreover, the pressure sensor 121 may be an analog or a digital pressure sensor.

The pressure sensor 121 may be operably coupled to the controller 105 and may send signals thereto, which may be based at least partially on the pressure detected in the exhaled gas in the exhalation line 120. In some embodiments, the controller 105 operate or direct operation of the supply valve 150 to increase or decrease the amount of fluid passing therethrough and/or the pressure of the fluid that actuates the diaphragm to define a suitable or selected opening through the diaphragm valve 110, such as to produce a suitable or selected pressure in the exhalation line 120 and in the lungs of the patient during exhalation.

In an embodiment, the controller 105 may substantially continuously operate or direct operation of the supply valve 150 and of the venting valve 170 to adjust the pressure in the exhalation line 120 and in the lungs of the patient to a selected pressure or to selected pressures that may vary from time to time or continuously. For example, as described above, the selected pressure may be input into the controller 105. The controller 105 may increase or decrease opening through the supply valve 150 and increase or decrease opening through the venting valve 170 to increase or decrease the opening through the diaphragm valve 110 (e.g., by changing the location of the diaphragm thereof) and to regulate the pressure applied to the lungs of the patient. For example, the controller 105 may close (or maintain closed) the venting valve 170 and at least partially open the supply valve 150 until the pressure sensor 121 detects the pressure in the exhalation line 120 to be the selected pressure. To reduce the pressure in the exhalation line 120 and in the lungs of the patient during exhalation (e.g., after the diaphragm valve 110 has been closed to a selected opening size), the controller 105 can operate or direct operation of the venting valve 170, such that the venting valve 170 permits venting of the fluids in the actuator line 140 to the atmosphere, thereby allowing the diaphragm of the diaphragm valve 110 to move to a location that defines and increased opening through the diaphragm valve 110, thereby reducing the pressure in the lungs of the patient.

In some embodiments, the PEEP system 100 may include an actuator line pressure sensor 141 in fluid communication with the actuator line 140 and configured to detect fluid pressure therein. Generally, the actuator line pressure sensor 141 may also be any suitable pressure sensor, such as a piezoelectric pressure sensor, pressure transducer, piezoresistive pressure sensor, capacitive pressure sensor, MEMS pressure sensor, LVDT pressure sensor, or combinations thereof. The actuator line pressure sensor 141 may be operably coupled to the controller 105 such that the controller 105 receives signals therefrom. For example, the controller 105 may operate and/or direct operation of the supply valve 150 at least partially based on the signals received at the controller 105 from the actuator line pressure sensor 141. In an embodiment, the controller 105 may be calibrated such that the controller 105 may operate the supply valve 150 at least partially based on the signals received from the actuator line pressure sensor 141 (e.g., the controller 105 may determine the signal to apply to the supply valve 150 based on a formula and/or lookup table that correlates the pressure in the actuator line 140 to the pressure in the exhalation line 120 (e.g., the formula or lookup table may correlate the opening of and/or the signal for the supply valve 150 to produce a selected pressure in the actuator line 140 and in the exhalation line 120).

In an embodiment, the source of pressurized fluid may supply the pressurized fluid to the supply valve 150 at approximately constant pressure (e.g., from about 5 psi to about 20 psi). For example, the flow of fluid through the supply valve 150 may be a sonic flow at a selected pressure or in a selected pressure range (e.g., 5-20 psi). In some embodiments, the pressure of the fluid flowing through the supply valve 150 may vary over time (e.g., the source of pressurized fluid may be a container, and the pressure of the fluid flowing through the supply valve 150 may drop as the fluid supply diminishes in the container).

Figure 2:
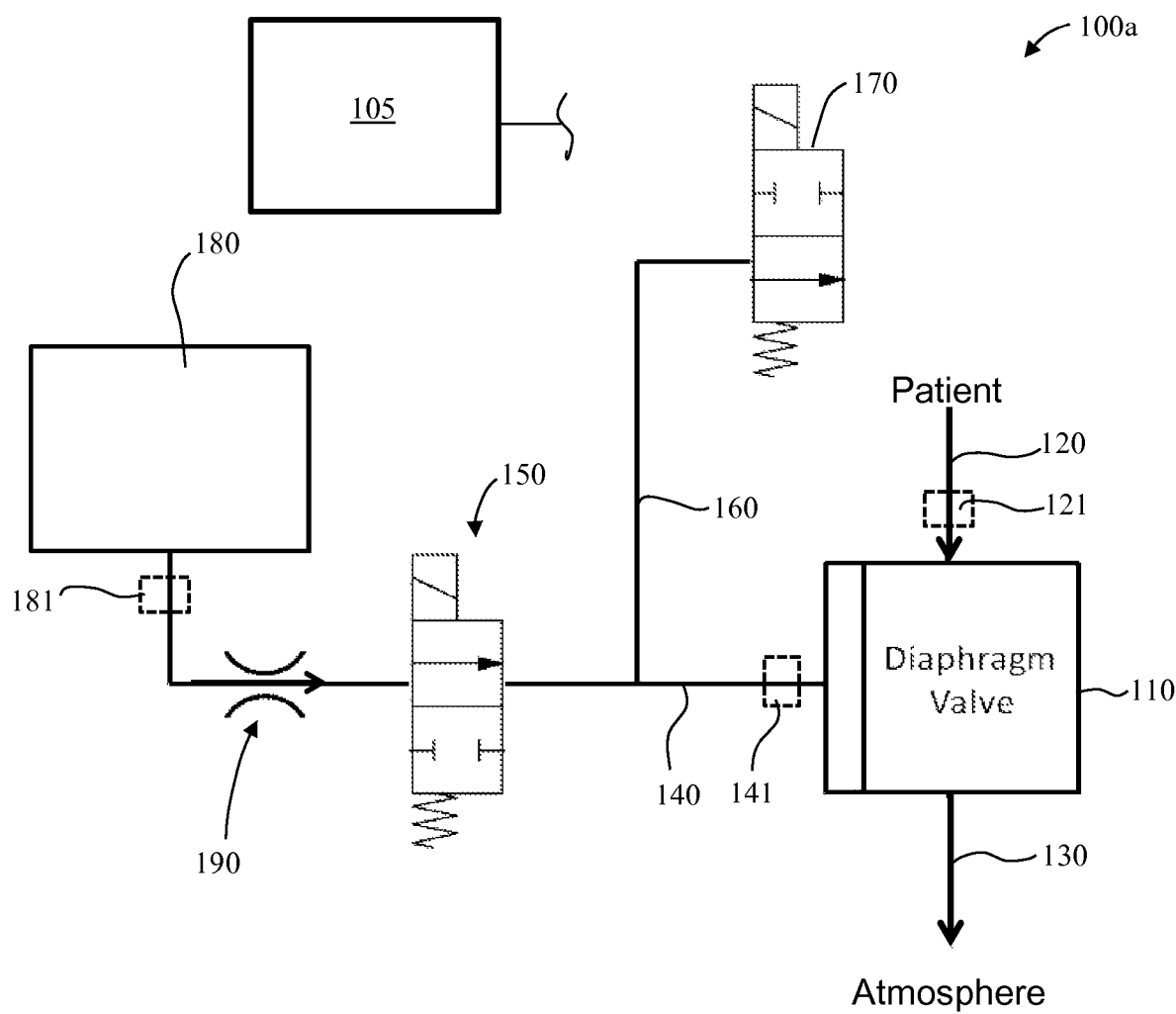
FIG. 2 is a schematic diagram of a system for applying positive end exhalation pressure to lungs of a patient, according to an embodiment.

FIG. 2 illustrates a PEEP system 100a that includes an accumulator 180 that may supply pressurized fluid, according to an embodiment. By way of example, the accumulator 180 may provide pressurized fluid having a selected fraction of inspired oxygen (FiO2) and may be part of any of the fluid blending systems disclosed in PCT International Application No. TBD filed concurrently herewith and titled "DEVICES, SYSTEMS, AND METHODS FOR MIXING AND BLENDING TWO OR MORE FLUIDS," the disclosure of which is incorporated herein, in its entirety, by this reference. For example, the fluid blending system may include or couple to two or more fluid sources and may mix and/or blend the fluids therefrom. The fluid blending system may control and/or regulate flow from of first fluid from a first source and/or flow of a second fluid from a second source. A controller that may operate or direct operation of one or more valves to control the flow of the first and second fluids, thereby producing a blended or mixed fluid that has selected concentrations or proportions (or ratios) of the first and second fluids for producing a breathable gas having a selected FiO2.

Except as otherwise described herein, the PEEP system 100a and its elements and components may be similar to or the same as the PEEP system 100 (FIG. 1). For example, the PEEP system 100a may include the diaphragm valve 110, exhalation line 120, outlet line 130, actuator line 140, supply valve 150, venting line 160, and venting valve 170 that may be similar to or the same as the corresponding elements of the PEEP system 100 (FIG. 1). Moreover, the PEEP system 100a may include the pressure sensors and the controller 105, which may be arranged and/or operably coupled in the same manners as the pressure sensors and the controller 105 described above in connection with the PEEP system 100 (FIG. 1). For example, the PEEP system 100a may include pressure sensor 121 in fluid communication with the exhalation line 120 and/or pressure sensor 141 in fluid communication with the actuator line 140.

The accumulator 180 may contain pressurized fluid (e.g., breathable gas) that may be supplied therefrom to the supply valve 150. As the fluid leaves the accumulator 180, the pressure therein may drop, and the pressure at the inlet of the supply valve 150 may, correspondingly, drop. In an embodiment, the PEEP system 100a may include an input fluid pressure sensor 181 in fluid communication with the accumulator 180 and/or with a location near or at the inlet of the supply valve 150. For example, the controller 105 may receive one or more signals from the input pressure sensor 181 and may operate or direct operation of the supply valve 150 at least partially based on the signal(s) received from the input pressure sensor 181 (e.g., such as to produce a selected or suitable pressure in the actuator line 140 and in the exhalation line 120).

In an embodiment, the PEEP system 100a may include an orifice 190 positioned between the accumulator 180 and the inlet of the supply valve 150. The orifice 190 may reduce the pressure of the fluid flowing therethrough by a suitable amount or percentage and/or to a suitable or selected pressure. For example, the fluid in the accumulator 180 may be pressurized to a relatively high pressure (e.g., 130 psi), and the orifice 190 may reduce the pressure of the fluid passing therethrough to a lower operating pressure (e.g., to 5-20 psi). Hence, for example, the orifice 190 may protect the supply valve 150 and/or the diaphragm valve 110 from fluid that may be at a pressure sufficiently high to damage the supply valve 150 and/or the diaphragm valve 110.

Figure 3:
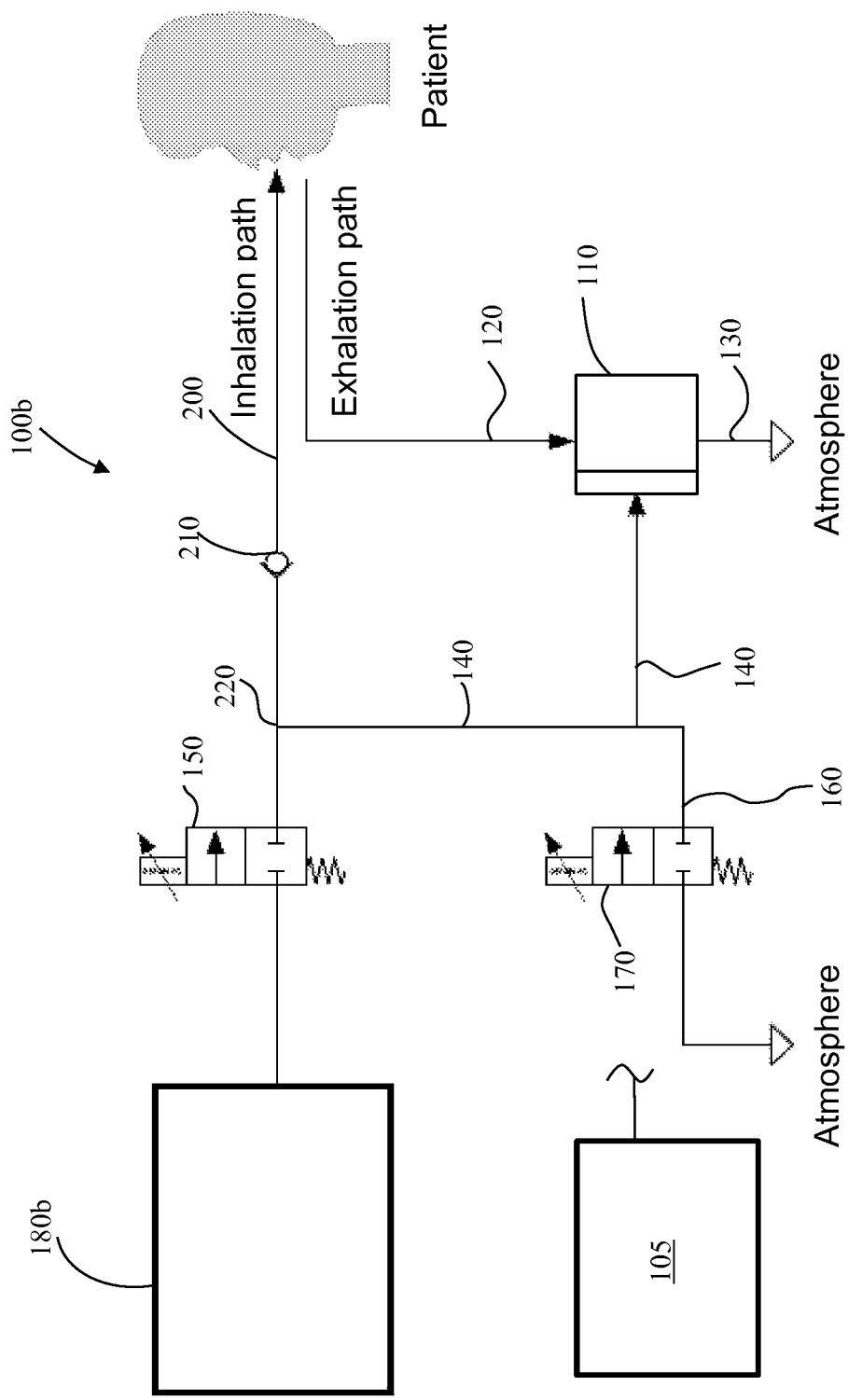
FIG. 3 is a schematic diagram of a system for applying positive end exhalation pressure to lungs of a patient, according to an embodiment.

As describe above, pressurized fluid that is used to operate or actuate the diaphragm valve may be a breathable gas (e.g., a gas that has a suitable percentage of Oxygen and/or other gases present in the air, such as Nitrogen). For example, the breathable gas may be a mixture or blend of Oxygen ($O_2$) and air, which may be taken from the atmosphere or surrounding environment. FIG. 3 is a schematic diagram of a PEEP system 100b that includes a source of pressurized breathable gas accumulator 180b, according to an embodiment. Except as otherwise described herein, the PEEP system 100b and its elements and components may be similar to or the same as any of the PEEP system 100, PEEP system 100a (FIGS. 1-2) and their corresponding elements and components. For example, in the illustrated embodiment, the accumulator 180b includes the diaphragm valve 110, exhalation line 120, outlet line 130, actuator line 140, supply valve 150, venting line 160, and venting valve 170 are arranged in as similar manner as corresponding components of the PEEP system 100 and PEEP system 100a (FIGS. 1-2). For example, the accumulator 180b may be the same or different as the accumulator 180 shown in FIG. 2 and may be part of a fluid blending system that supplies pressurized fluid having a selected FiO2.

In an embodiment, the PEEP system 100b may supply the breathable gas from the accumulator 180b to the patient. That is, the patient may inhale or breathe in the breathable gas supplied from the accumulator 180b. For example, the breathable gas may flow from the accumulator 180b, through the supply valve 150, and into an inhalation line 200, from which the breathable gas may be provided to patient. Moreover, as described above, the pressurized breathable gas may flow from the supply valve 150 into the actuator line 140 to operate (e.g., at least partially open and/or close) the diaphragm valve 110. In some embodiments, when the pressurized breathable gas enters the actuator line 140 and the inhalation line 200, the pressure of the breathable gas may be suitable or sufficient to at least partially close that diaphragm valve 110 (as the breathable gas in the actuator line 140 applies pressure on the actuator and on the diaphragm of the diaphragm valve 110) and to supply breathable gas to the patient from the inhalation line 200.

In other words, the patient may breathe in the breathable gas from the accumulator 180b, while the diaphragm valve 110 may be closed by the pressure applied to the actuator of the diaphragm valve 110 by the breathable gas. In some embodiments, the PEEP system 100b may include an optional check valve 210 that may prevent flow of gas from the patient toward the supply valve 150. In particular, for example, the check valve 210 may be positioned along the inhalation line 200 between the supply valve 150 and the patient. As such, for example, as the patient exhales, the exhaled gas may flow from the patient in the exhalation line 120 toward the diaphragm valve 110, as described above.

In some embodiments, the diaphragm valve 110 may have a mechanical advantage such that to close the diaphragm valve 110 and prevent gas flow out of the exhalation line 120, a pressure applied on the actuator side of the diaphragm valve 110 by the pressurized breathable gas in the actuator line 140 may be lower than the pressure in the lungs of the patient and in the exhalation line 120. In other words, the mechanical advantage of the diaphragm valve 110 may prevent airflow from the exhalation line 120 and through the diaphragm valve 110 as the air is supplied from the inhalation line 200 into the lungs of the patient. Generally, the mechanical advantage of the diaphragm valve 110 may vary from one embodiment to the next. For example, the mechanical advantage of the diaphragm valve 110 may be 1.5:1 (e.g., to close the diaphragm valve 110, the pressure on the actuator side of the diaphragm valve 110 may be 1.5 times lower than in the exhalation line 120), 2:1, etc.

Additionally or alternatively, the PEEP system 100b may include an orifice positioned along the inhalation line 200 and past a junction 220 between the inhalation line 200 and the actuator line 140. Hence, in an embodiment, the orifice may reduce the pressure in the inhalation line 200, such that the pressure in the inhalation line 200 is lower than the pressure in the actuator line 140. For example, the pressure in the inhalation line 200 may be suitable for inflating the lungs of the patient, while the pressure in the actuator line 140 may be suitable for closing the diaphragm valve 110, such that the breathable gas that enters the lungs of the patient does not exit therefrom through the exhalation line 120 before exhalation begins.

In an embodiment, the controller 105 may operate or direct operation of the supply valve 150 and the venting valve 170 to apply positive and exhalation pressure to the lungs of the patient. For example, the controller 105 may selectively at least partially close and/or open the diaphragm valve 110 in a manner that applies suitable pressure to the lungs of the patient, as described above.

Figure 4:
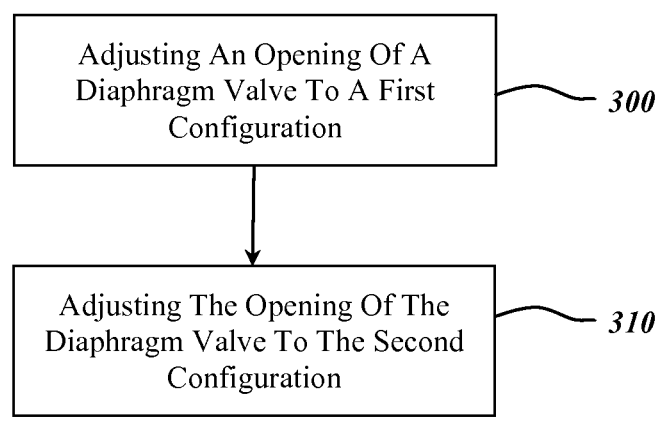
FIG. 4 is a flow chart of a method for applying positive end exhalation pressure to lungs of a patient, according to an embodiment.

FIG. 4 is a flow chart of acts of a method for applying positive end exhalation pressure to the lungs of the patient, according to an embodiment. It should be appreciated that the acts described herein may be performed by or with a system according to one or more embodiments described herein. In an embodiment, the method may include an act 300 of adjusting an opening of a diaphragm valve, which is coupled to an exhalation line, to a first configuration. The exhalation line may be in fluid communication with the lungs of the patient, and the exhaled gas from the lungs flows in the exhalation line to atmosphere. For example, in the first configuration, the diaphragm valve may be positioned to define at least partially closed opening through the diaphragm valve. As described above, partially closing the diaphragm valve may apply positive end exhalation pressure on the lungs of the patient.

The method also may include an act 310 of adjusting the opening of the diaphragm valve to a second configuration. In an embodiment, when the diaphragm valve is in the second configuration, the opening therethrough may be greater than the opening in the first configuration. For example, the diaphragm valve may be fully open in the second configuration. When the diaphragm valve is in the second configuration, the positive end exhalation pressure applied to the lungs of the patient may be lower than the pressure applied thereto when the diaphragm valve is in the first configuration.

A controller may perform the acts 300 and 310 and/or may direct performance thereof substantially continuously and/or in any number of suitable sequences to adjust the pressure applied to the lungs of the patient. Moreover, the pressure produced in the lungs of the patient after the act 300 may be any suitable or selected pressure, which may vary from one embodiment to another and/or from one iteration to another. The pressure produced in the lungs of the patient after the act 310 may be any suitable or selected pressure, which may vary from one embodiment to another and/or from one iteration to another.

It should be also appreciated the opening of the diaphragm valve before or after adjustment thereof to the first or second configuration may be any suitable opening, which may vary from one embodiment to the next. In some embodiments, the diaphragm valve may be fully closed before or after adjustment thereof to the first or second configuration. Moreover, the diaphragm valve may be partially or fully open before or after adjustment thereof to the first or second configuration.

In an embodiment, the diaphragm valve may be closed at the start of exhalation to produce a suitable pressure in the lungs of the patient. After the pressure in the lungs of the patient reaches a suitable or selected level, the diaphragm valve may be at least partially opened to maintain the pressure in the lungs of the patient at the selected level or to reduce the pressure. For example, when the controller receives a signal from a pressure sensor that is in fluid communication with the exhalation line, and the received signal is at or near a selected value (or corresponds with a pressure that is near or at the value of the selected pressure), the controller may operate or direct operation of the supply valve and/or of the vent vale in a manner that at least partially opens the diaphragm valve. It should be appreciated that, under some operating conditions, the operation of the supply and vent valves may be generally synchronized and may result in faster operation (e.g., opening and closing) of the diaphragm valve (e.g., as compared to the operation of the diaphragm valve that may be produced by operating only the supply valve).

While various aspects and embodiments have been disclosed herein, other aspects and embodiments are contemplated. The various aspects and embodiments disclosed herein are for purposes of illustration and are not intended to be limiting.

We claim:

1. A system for applying positive end expiratory pressure (PEEP) in ventilation of lungs of a patient, the system comprising:
   an exhalation line configured to be in fluid communication with the lungs of the patient and to receive exhaled gas from the lungs of the patient;
   a diaphragm valve having an actuator and a diaphragm, the diaphragm valve coupled to the exhalation line and configured to restrict fluid flow therefrom, thereby applying positive end expiratory pressure during exhalation of air from the lungs of the patient, in response to a control pressure applied at the actuator of the diaphragm valve;
   an actuator line coupling the diaphragm valve to a source of pressurized fluid with the diaphragm valve between the exhalation line and the actuator line;
   an electrically-controllable valve coupled to the actuator line and controlling the pressure applied by fluid from the source of pressurized fluid to the actuator of the diaphragm valve effective to control a position of the actuator and the diaphragm in the diaphragm valve;
   an outlet line coupled to the diaphragm valve and in fluid communication with approximately atmospheric pressure, the diaphragm valve being positioned between the exhalation line and the outlet line; and
   a controller operably coupled to the electrically-controllable valve and configured to change the positive end expiratory pressure by directing operation of the electrically-controllable valve.

2. The system of claim 1, further comprising the source of pressurized fluid coupled to the electrically-controllable valve.

3. The system of claim 1, further comprising one or more pressure sensors in fluid communication with the exhalation line and operably coupled to the controller, which is configured to direct operation of the electrically-controllable valve at least partially based on signals received from the one or more pressure sensors.

4. The system of claim 3, further comprising a vent valve in fluid communication with one or more of the actuator line or the diaphragm valve via a venting line and, when at least partially open, configured to reduce pressure applied to the actuator of the diaphragm valve, wherein the diaphragm valve is positioned between the exhalation line and the venting line.

5. The system of claim 4 wherein the vent valve is operably coupled to the controller and configured to direct operation of the vent valve at least partially based on the signals received from the one or more pressure sensors.

6. The system of claim 4 wherein the controller is configured to receive input from a user, the input being related to a selected positive end expiratory pressure to apply to the lungs of the patient, the controller directing operation of one or more of the electrically-controllable valve and the vent valve.

7. The system of claim 1 wherein:
   when the diaphragm valve is in a fully open configuration, the exhaled gas in the exhalation line is at the approximately atmospheric pressure; and
   the diaphragm valve includes a passageway having a cross-sectional area that is equal to or greater than a cross-sectional area of at least one of the exhalation line or the outlet line.

8. The system of claim 1 wherein the diaphragm valve is disposable.

9. A system for applying positive end expiratory pressure (PEEP) in ventilation of lungs of a patient, the system comprising:
   an exhalation line configured to be in fluid communication with the lungs of the patient and to receive exhaled gas from the lungs of the patient;
   a pressure-operated valve coupled to the exhalation line and configured to restrict fluid flow therefrom, thereby applying positive end expiratory pressure during exhalation of air from the lungs of the patient, in response to a control pressure applied on an actuator of the pressure-operated valve;

an actuator line coupling the pressure-operated valve control to a source of pressurized breathable gas and configured to supply the pressurized breathable gas to apply the control pressure on the actuator of the pressure-operated valve with the pressure-operated valve between the exhalation line and the actuator line;

an inhalation line coupleable to the source of pressurized breathable gas to supply the breathable gas into the lungs of the patient;

an outlet line coupled to the pressure-operated valve and in fluid communication with approximately atmospheric pressure, the outlet line being downstream from the pressure-operated valve and the exhalation line such that the exhaled gas flows from the exhalation line, through the pressure-operated valve, and out the outlet line; and a supply valve coupleable to the source of pressurized breathable gas and coupled to the actuator line and to the inhalation line and configured to control supply of the pressurized breathable gas to the actuator line and the inhalation line.

10. The system of claim 9 wherein the pressure-operated valve includes a disposable diaphragm valve.

11. The system of claim 10 wherein the controller is further configured to direct operation of the supply valve to control the pressure-operated valve and the pressure in the exhalation line.

12. The system of claim 11, further comprising a pressure sensor configured to generate one or more signals related to the pressure of the exhaled gas in the exhalation line, the controller being operably coupled to the pressure sensor and configured to receive the signals therefrom and to direct operation of the supply valve at least partially based on the signals from the pressure sensor.

13. The system of claim 9, further comprising a controller operably coupled to the supply valve and configured to direct operation of the supply valve to control supply of the breathable gas from the inhalation line to the lungs of the patient.

14. The system of claim 9, further comprising a vent valve in fluid communication with the inhalation line and in fluid communication with one or more of the actuator line or the pressure-controlled valve via a venting line, wherein, when at least partially open, the vent valve being configured to reduce pressure of the breathable gas in the one or more of the inhalation line or the actuator line, the pressure-controlled valve being positioned between the exhalation line and the venting line.

15. The system of claim 9, further comprising a check valve positioned along the inhalation line between the supply valve and the patient and configured to prevent or limit flow in the inhalation line away from the patient.

16. The system of claim 9, further comprising an electrically-controllable valve configured to control the pressure applied by fluid from the source of pressurized fluid to the actuator of the pressure-operated valve.

17. The system of claim 9, further comprising the source of pressurized breathable gas coupled to the supply valve.

18. A method for controlling application of positive end expiratory pressure (PEEP) in ventilation of lungs of a patient, the method comprising:

placing a pressurizable channel in fluid communication with the lungs of the patient for accepting exhaled gas therefrom;

operating a pressure-controllable valve to control flow of the exhaled gas in the pressurizable channel by applying pressure from an actuator line at an actuator of the pressure-controllable valve, the pressure controllable valve located between the actuator line and the pressurizable channel;

placing an outlet line in fluid communication with approximately atmospheric pressure and coupled to the pressure-controllable valve with the outlet line being downstream from the pressure-controllable valve and the pressurizable channel such that the exhaled gas flows from the pressurizable channel, through the pressure controllable valve, and out the outlet line; and controlling a solenoid valve to apply the pressure at the actuator of the pressure-controllable valve.

19. The method of claim 18 wherein controlling the solenoid valve regulates flow of a fluid from a source of pressurized fluid, and the pressurized fluid applies the pressure to the actuator of the pressure-controllable valve effective to control a position of the actuator of the pressure-controllable valve.

20. The method of claim 19 wherein the pressurized fluid includes a breathable gas.

21. The method of claim 20 wherein controlling the solenoid valve further includes supplying the breathable gas into the lungs of the patient.

22. The method of claim 18 wherein the solenoid valve includes a proportional solenoid valve and wherein controlling a solenoid valve includes varying a signal applied to the proportional solenoid valve.

23. The method of claim 18, further comprising selectively venting the fluid applying pressure to the actuator of the pressure-controllable valve, thereby reducing pressure in the pressurizable channel.

\* \* \* \* \*